(12) United States Patent
Lee et al.

(10) Patent No.: US 6,432,451 B1
(45) Date of Patent: Aug. 13, 2002

(54) FILM COATED MICROBEADS CONTAINING ACTIVE COMPOUNDS AND METHOD OF MAKING THE SAME

(75) Inventors: Jang Young Lee, Seoul; Soon Sang Guan, Kyungki-do; Jin Han Kim, Seoul; Jong Won Park; Moon Jae Choi, both of Kyungki-do; Yu Chang Kim, Seoul, all of (KR)

(73) Assignee: Pacific Corporation, Seoul (KR)

( * ) Notice: Subject to any disclaimer, the term of this patent is extended or adjusted under 35 U.S.C. 154(b) by 0 days.

(21) Appl. No.: 09/553,653

(22) Filed: Apr. 21, 2000

(30) Foreign Application Priority Data

Apr. 23, 1999 (KR) ........................................ 99-0014660

(51) Int. Cl.⁷ ............................ A61K 9/16; A61K 9/14; A61K 9/50

(52) U.S. Cl. ..................... 424/490; 424/489; 424/484; 424/501

(58) Field of Search ................................ 424/489, 484, 424/501, 419, 81, 490; 521/54

(56) References Cited

U.S. PATENT DOCUMENTS 5,073,365 A * 12/1991 Katz et al. .................. 424/489
5,246,972 A * 9/1993 Cifuentes et al. ............. 521/54

* cited by examiner

*Primary Examiner*—Thurman K. Page
*Assistant Examiner*—Blessing Fubara
(74) *Attorney, Agent, or Firm*—Knobbe Martens Olson & Bear LLP.

(57) ABSTRACT

Disclosed is a composition for use in dermal application. The composition includes microbeads or chemically stable particles having an internal structure of pores. A chemical compound having a pharmaceutical or cosmetic activity is retained in the internal structure of the porous particles. Each of the particles is coated with at least one of a silicone and a polysiloxane-based compound. Also disclosed is a method of making a composition. A plurality of particles containing a chemical compound in its internal structure is prepared. A coating mixture including at least one of a silicone and a polysiloxane-based compound with a solvent is also prepared. The particles are mixed with the coating mixture, which coats over the particles. The coated particles are subject to drying to evaporate the solvent from the coating mixture.

18 Claims, No Drawings

FILM COATED MICROBEADS CONTAINING ACTIVE COMPOUNDS AND METHOD OF MAKING THE SAME

BACKGROUND OF THE INVENTION

1. Field of the Invention

The present invention relates generally to a method for film coating the surface of porous micro beads having pores containing active components with silicone or its derivatives, and cosmetic and pharmaceutical compositions for dermal application containing porous micro beads silicone-coated by the film coating method.

2. Description of the Related Art

Ingredients such as vitamins, antioxidants and enzymes are known to have effects of, for example, whitening, wrinkle clearing, increasing skin's elasticity, noxious oxygen removing, etc. and have been widely used as active components of cosmetic and pharmaceutical compositions for dermal application. However, when exposed to light or air, the active components are susceptible to oxidation and destruction and thus limited in their applications. Oxidation of the active components causes not only a deterioration of potency but also discoloration, for example, browning or yellowing depending on the type of the active components.

Such an oxidative destruction accelerates for active components that are present in an aqueous phase or in contact with water.

In connection to this, there have been suggested a number of methods for stabilization of the active components by minimizing contact of the active components with water.

A method for formulating active components into dry powder (see. Japanese Patent Application Laid-open So 63-130514) is effective in maintaining stability of the active components to a certain extent but confined in formulation to powder. Thus the method is inapplicable to general cosmetic compositions of which the typical formulation is emulsion.

In an alternative method to cope with the problem, two separate containers are packed with powdery active components and an emulsified cosmetic liquid, respectively, for the user to mix prior to application (see. U.S. Pat. No. 4,818, 512). However, this method is problematic in regard to inconvenience for the user who has to mix the contents of the two containers before use, and high expense of the packages.

An anhydrous formulation containing no moisture (see. U.S. Pat. No. 5,322,683) may retain stability of active components but is confined to powder. Also, the anhydrous formulation gives an unpleasant feeling to the skin because of its greasy property and is especially inapplicable to water soluble active components.

There have been proposed further another methods involving addition of polyhydric alcohols such as glycerin, or other organic solvents compatible with water (see. U.S. Pat. Nos. 5,703,041 and 4,983,382; JP Patent No. 44-22312; and U.S. Pat. No. 4,372,874). These methods stabilize the active components to a certain extent but give an unpleasant feeling to the skin due to its stickiness peculiar to polyhydric alcohols. Especially, organic solvents useful for stabilization of the active components, such as dimethylsulfoxide are normally toxic to the human body.

Besides, a method has been reported to utilize microcapsules and stabilize active components with a physical layer formed on the outer surface of the active components (Simon Benita (ed), 1996, Microencapsulation: Methods and industrial applications, Marcel Dekker, Inc. New York). The microcapsules are however unsatisfactory to achieve complete stabilization of the active components, because the coating on the wall material constituting the microcapsules permits entrance of water and allows active components to dissolve out through diffusion.

An alternative method involves retaining active components in the pores of porous microbeads in the same manner as the previously stated microcapsules (William Klein and Alfred DiSapio, 1989, HAPPI magazine, 26:7; U.S. Pat. No. 5,145,675). In contrast to the microcapsules where the capsule constituents provide a complete physical separation of the internal phase of the capsules from the external one, the porous microbeads have the internal phase in communication with the external one through pores containing active components.

SUMMARY OF THE INVENTION

One aspect of the present invention provides a composition for use in dermal application. The composition comprises a plurality of particles having an internal structure of pores, a chemical compound contained in the internal structure of the porous particles, and a layer of coating over each of the particles, containing at least one of a silicone and a polysiloxane-based compound.

Another aspect of the present invention provides a method of making a composition. The method comprises the steps of: preparing a plurality of particles containing a chemical compound in an internal structure thereof; preparing a coating mixture comprising at least one of a silicone and a polysiloxane-based compound with a solvent; mixing the plurality of particles with the coating mixture, whereby the coating mixture covering over the particles; and evaporating the solvent from the coating mixture covering over the particles.

DETAILED DESCRIPTION OF THE INVENTION

In the microbead system retaining active ingredients within the pores, the stability and efflux of the active ingredients significantly depend upon their physiochemical properties and the ambient solvent constituting the internal phase as well as those of the outer base constituting the external phase due to communication between internal and external phases. For example, if the active components adsorbed in the pores or the solvent dissolving the active components within the pores have high affinity to the base of the external phase, the active components are susceptible to effusion and their stability deteriorates significantly. Thus, the internal phase of the pores must not have affinity to the base of the external phase in a composition containing active components.

Especially, in order to stabilize active components susceptive to water, the active components must have minimized contact with water while they are contained in the pores. However, a general cosmetic composition has the formulation of emulsion containing a large amount of surfactant such that two solvents naturally immiscible with each other, such as water and oil, are mixed together in no small amount. Thus, the stability of the active components in a cosmetic composition actually depends upon the physiochemical properties of the active components and the external base.

According to one aspect of the present invention, active ingredients of a cosmetic or pharmaceutical composition are retained in the internal structure of porous particles or microbeads. Thereafter, the particles or microbeads containing the active ingredients are coated with a thin film of a material.

First, active ingredients of a cosmetic or pharmaceutical composition are dissolved in a solvent selected from the group consisting of methanol, ethanol, glycerin alone, and mixtures thereof. The resulting solution or suspension is subject to physical contact with porous particles or microbeads to retain the active components in their internal structure of pores. The porous microbeads retaining the active components are separated from the solution or suspension by filtration. The residual solvent of the microbeads is removed and the active components impregnated within the internal structure of the microbeads by subsequent vacuum drying and washing processes.

The porous particles or microbeads have an internal structure of interconnected matrix structure, in which the active components are retained or impregnated. The active ingredients effuse from internal structure by capillary action when the porous particles or microbeads are applied to skin or other surfaces.

The porous microbeads usable in the present invention are prepared through formation of pores with three-dimensional cross-links of a polymer or copolymer. Examples of the polymer or copolymer include, but are not limited to polymethacrylic acid copolymer, polymethylmethacrylic acid copolymer, allyl-polymethacrylic acid copolymer, polystyrene polymer, polyethylcellulose polymer, and silicagel. All the polymers or copolymers are commercially available as well as porous microbeads formed from the three-dimensional cross-links thereof and, of course, may be chemically synthesized by those skilled in the art.

Preferably, the porous microbeads are about 1~500 μm in diameter and 5~50 μm in diameter distribution.

Higher porosity of the particles or microbeads would be better to retain a higher amount of the active components, but may incur relative deterioration of the mechanical strength of the porous microbeads, which is problematic in preparation of the composition containing the porous microbeads. It is thus preferable that the porous microbeads are chosen in accordance with the characteristics based on the workability of the formulation and the degree of retainment of the active components.

As the pores of the porous microbeads formed through three-dimensional cross-links of the polymer are typically less than 0.5 μm in size, the active components are difficult to adsorb in the pores if they are not in the solution state. The solvent for dissolving the active components has to meet the following requirements: (1) well dissolving a large amount of active components; (2) not inhibiting retainment of the active components in the pores; and (3) if toxic to human body or irritative to the skin, easiness of removal after retaining the active components in the particles or microbeads.

Examples of the solvent suitable for use in retaining the active components in the pores of the porous microbeads include methanol and ethanol, which are capable of dissolving almost water-soluble and fat-soluble active components of high content and easily removable by a known method such as drying.

As the solvent, glycerin may reduce retaining rate of the active components due to its high viscosity but exhibits high solubility for water-soluble active components such as L-ascorbic acid, without incurring stimuli to the skin.

Retaining the active components in the pores of the porous microbeads is typically achieved through a physical contact of the porous microbeads with a solution of the active components. Any methods for facilitating the retainment of the active components in the pores can be used, such as stirring or heating the dispersed solution of the porous microbeads or addition of a surfactant. A known method to retain chemicals in porous microbeads is disclosed in HAPPI magazine, 1989, 26:7 by William Klein and Alfred DiSapio and in U.S. Pat. No. 5,145,675, which are hereby incorporated herein by reference. According to the disclosure, the adsorption rate of the active components per unit weight of the porous microbeads varies depending on the properties of the active components and the type of the solvent. For L-ascorbic acid, for example, the adsorption rate is about 20~90 wt. % when using one of the above-mentioned solvents alone, or mixtures thereof.

After retaining the active components in the pores, the porous microbeads are separated through a filtration and then washed in order to remove a residual solution of the active components on the surface of the porous microbeads and among the granules of them. An excess of the solution remaining on the surface of the porous microbeads and among the granules of them may not only inhibit the film coating process of the present invention later described, but also deteriorate stability of the active components through effusion, in case of cosmetic and pharmaceutical compositions.

The washing solvent as used herein has to meet the following requirements: low solubility to the active components and high compatibility with the solvent of the solution containing the active components. A suitable washing solvent is isopropanol or acetone for L-ascorbic acid.

The washing process includes adding the washing solvent to the filter cake of the porous microbeads obtained by filtration, and performing a second filtration. Alternatively, the washing process includes, if necessary, separate removal of the filter case, dispersing the separated filter cake in the washing solvent for washing, and then performing a second filtration. The former method is usually preferred because excessive washing of the filter cake may lead to a loss of the active components retained by the pores.

For removal of the residual solvent in the pores after the washing process, the porous microbeads are dried under atmospheric pressure or vacuum. The drying process typically completes within one day under vacuum but the drying period may be varied depending on the volatility of the solvent. For methanol as the solvent, the drying period is usually one day under vacuum.

After the completion of washing and drying, the porous microbeads have the form of powdery solid. The active components remain in the solid state within the pores if the solvent is completely removed through the drying process, or in the state of supersaturated solution if part of the solvent resides in the pores.

At this stage, addition of the porous microbeads to an emulsified or dispersed cosmetic composition results in significant deterioration of the stability of the active components that are compatible with the external base, since the active components adsorbed by the porous microbeads are ready to effuse. For example, in a case where porous microbeads containing L-ascorbic acid (vitamin C) very soluble in water is added to a normal water-in-oil type emulsion, L-ascorbic acid becomes in contact with water as the external phase and easily effuses, thereby resulting in abrupt deterioration of the stability.

To prevent such a deterioration of the stability of the active components, the present invention film coats the surface of the porous microbeads adsorbing the active components with an appropriate compound for preventing water penetration into the surface of the porous microbeads.

The film coating for this purpose has not to permanently inhibit communication between the exterior and interior of the pores of the porous microbeads.

A permanent film coating of the pores to block the communication between the exterior and interior of the pores may increase stability of the active components but cannot realize efficacy of the active components in a cosmetic or pharmaceutical composition because the active components cannot effuse from the pores when applied to the skin.

The inventor of this invention selects silicone and its derivatives as a film coating agent. Silicone and its derivatives present some advantages including: (1) water repellency sufficient to prevent penetration of water into the pores; (2) immiscibility with almost cosmetic oils; (3) commercial availability; (4) strong binding force with the porous microbeads by way of reactive functional groups for effective film coating; and (5) innoxiousness to the human body.

Hereafter, a description will be made in detail as to a film coating method for the above-prepared porous microbeads containing active components with silicone or its derivatives. There are two methods for film coating the porous microbeads with silicone or its derivatives.

The one method involves using a mixture of silicone as a film coating agent and an organic solvent of high melting capacity for silicone, high volatility and low melting capacity for active components.

Examples of the silicone suitable for the above purpose include methicone, dimethicone, dimethicone copolyol and its derivatives, dimethiconol and its derivatives, and a variety of copolymers, with dimethicone being most preferred.

Examples of the volatile organic solvent include dichloromethane, chloroform, ethyl acetate, and acetone, with dichloromethane being most preferred.

The silicone is preferably added in a range of about 5~50 wt. %, based upon the total weight of the porous microbeads for film coating. With the silicone content less than 5 wt. %, the obtained porous microbeads are incompletely film coated. In contrast thereto, the film coating is excessively thickened or silicone oil aggregates not adsorbed by the surface of the porous microbeads occur with the silicone content greater than 50 wt. %.

The volatile solvent is added in such an appropriate amount as to maintain fluidity after dispersion of the porous microbeads.

The porous microbeads containing the water soluble active components are dispersed in a mixed solution of the silicone and the volatile solvent, and thereafter, the resulting mixture is subjected to drying or vaporization under atmospheric pressure or vacuum while stirring. Thus the volatile solvent is removed and the silicone aggregates on the surface of the porous microbeads to form a silicone film.

Upon vaporization of almost the volatile solvent, film coated porous microbeads are obtained in the form of powder. Then, drying is performed under vacuum in order to completely remove the volatile solvent.

The other method for film coating the porous microbeads with silicone or its derivatives involves using a mixture of a polysiloxane-based compound as a film coating agent, with optionally a silane-based compound.

The polysiloxane-based compound suitable for use in this method is usually polydimethylsiloxane-based derivatives and has reactive functional groups at both terminals or an intermediate portion of the straight chain. Hardening occurs due to cross-linking of the polysiloxane-based compound alone or together with the silane-based compound. The reactive functional groups are hydroxyl (—OH), chloride (—Cl), and hydrogen (—H) and directly bonded to silicone (Si) of polysiloxane. For the reactive functional group, the hydroxyl group or chloride is usually located at both terminals of the polymethylsiloxane chain, and the hydrogen is located at the intermediate portion as well as both terminals of the chain, in which case the compound is called poly (dimethylsiloxane-co-methylhydrosiloxane). Methylhydrosiloxane monomers containing hydrogens are preferably present in an amount of less than 20% based on the total weight of the copolymer. This is because, in a case of incomplete reaction, the higher hydrogen content sometimes causes the film coated porous microbeads to react with water contained in the final product such as cosmetic compositions and generate hydrogen gas.

The silane-based compound is an alkoxysilane compound containing three or four ethoxyl groups and, the examples thereof include tetramethoxy silane, tetraethoxysilane, methyltrimethoxysilane, —methacryloxypropyltrimethoxysilane, —and glycydoxypropyltrimethoxysilane.

The reaction mechanism can be expressed by the reaction formula 1:

[Reaction Formula 1]

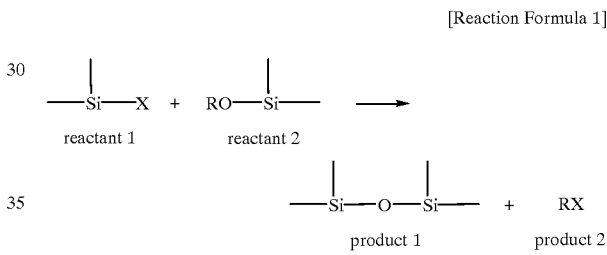

In the reaction formula 1, R of the reactant 2 is methyl or ethyl when X of the reactant 1 is hydroxyl (—OH), or solely H when X of the reactant 1 is H or Cl; the reactant 1 represents a reactive polysiloxane-based compound; and the reactant 2 represents a silane-based compound wherein R of the reactant 2 is methyl or ethyl, or a polysiloxane-based compound wherein R of the reactant 2 is H.

The silane-based compound reacts with three or four polysiloxane molecules in the above mechanism and serves as a cross-link agent. The silane-based compound has to be added during formation of the film coating when the porous microbeads are free from a reactive functional group such as a hydroxyl group on. The porous microbeads having hydroxyl groups, such as silicagel may participate in direct reaction with the reactive functional groups of the polysiloxane, in which case the film coating can also be formed with a reactive polysiloxane-based compound alone or mixtures thereof.

A solvent for dissolving the polysiloxane-based compound and the silane-based compound is selected depending upon the desired types of polysiloxane-based compound and the silane-based compound and the active compounds adsorbed by the porous microbeads. Typically, the suitable solvent is an organic solvent for water-soluble active components, and used in the form of a water-in-oil type emulsion for fat-soluble active components.

A detailed description will be given below to a film coating method using a mixture of a polysiloxane-based compound and optionally a silane-based compound.

A silicone mixture of a reactive polysiloxane-based compound alone or a mixture of at least two reactive polysiloxane-based compounds, and optionally a silane-based compound is dissolved in an organic solvent such as dichloromethane or chloroform, or in the form of a water-in-oil type emulsion. The silane-based compound is preferably present in an amount of less than 10% of the reactive polysiloxane-based compound. An excess of the silane-based compound decreases polymerization degree with excessively increased consistency of the film and remains substances that have not been participated in the reaction, thereby adversely affecting the skin. If necessary, a catalyst such as zinc octoate and dibutyltin dilaurate is added in an amount of about 0.1~4 wt. % based on the total weight of the polysiloxane-based compound. Thereafter, porous microbeads retaining active components are added and stirred for 2~3 hours for uniform mixing. The added amount of the reactive polysiloxane-based compound is in the range of about 1~100 wt. % based on the total weight of the porous microbeads since the porosity depends on the type of the porous microbeads. The mixture is heated in a reactor with a condenser under stirring, while maintaining at 40° C. to evaporate the solvent. The resulting porous microbeads are maintained at the room temperature for about three days to remove the residual solvent. The porous microbeads are in some cases washed with a solvent such as isopropanol in order to remove substances that have not been participated in the reaction.

The second film coating method maintains a predetermined distance between the film and the surface of the porous microbeads and therefore promotes water repellency of the porous microbeads. Thus the film coating process is practicable prior to adsorption of the active components so that the biological active components such as enzymes can be stabilized during in contact with an organic solvent or oils.

Hereinafter, the present invention will be illustrated in detail in terms of structure and operation by way of examples, but not limited thereto.

1. PREPARATION OF POROUS MICROBEADS CONTAINING ACTIVE COMPONENTS

EXAMPLE 1

Preparation of porous microbeads containing retinol.

500 ml of pure retinol was dissolved in squalane to give the retinol solution in a concentration of 300,000 IU per 1 g of the solution. 10 g of porous microbeads composed of three-dimensional cross-links of allyl-polymethacrylic acid copolymer was added to the retinol solution and completely dispersed under slow stirring. The resulting dispersion solution was filtered to separate the porous microbeads. Thereafter, drying under vacuum gave porous microbeads containing retinol in a concentration of 66,000 IU/g.

EXAMPLE 2

(1) Preparation of porous microbeads containing L-ascorbic acid.

L-ascorbic acid powder was dissolved in methanol to give 500 ml of the L-ascorbic acid solution containing 7 wt. % of L-ascorbic acid. 10 g of porous microbeads composed of three-dimensional cross-links of allyl-polymethacrylic acid copolymer was added to the L-ascorbic acid solution and completely dispersed under slow stirring. The resulting dispersion solution was filtered to separate a filter cake of the porous microbeads, which was then washed with 1 liter of acetone. Thereafter, drying under vacuum gave powdery porous microbeads containing crystalline L-ascorbic acid. For increasing the L-ascorbic acid content of the porous microbeads, the above procedure was repeated three times to yield porous microbeads containing 45 wt. % of L-ascorbic acid.

EXAMPLE 3

(2) Preparation of porous microbeads containing L-ascorbic acid.

L-ascorbic acid powder was dispersed in a mixed solution of glycerin and ethanol to give a dispersion solution containing 30 wt. % of L-ascorbic acid. 40 wt. % of ethanol was present in the mixed solution. Generally, the ethanol content higher than 40 wt. % decreases the solubility of L-ascorbic acid and the ethanol content lower than 40% makes it difficult to separate the porous microbeads through filtration after adsorption of L-ascorbic acid. The dispersion solution was heated to 75° C. to increase the solubility of L-ascorbic acid and yield a clear L-ascorbic acid solution. Nitrogen was successively added to the reactor in order to prevent decomposition of L-ascorbic acid due to oxidation under the hot condition. And, the ethanol was recycled after installation of a condenser for preventing a loss of the ethanol through vaporization under the hot condition. Porous microbeads composed of three-dimensional cross-links of allyl-polymethacrylic acid copolymer was then added to the dispersion solution containing L-ascorbic acid and completely dispersed under slow stirring. Here, the added amount of the porous microbeads was equivalent to the initial amount of the L-ascorbic acid powder. The resulting dispersion solution was filtered to separate the porous microbeads, which was then washed with acetone. Drying under atmospheric pressure or vacuum gave powdery porous microbeads containing liquid L-ascorbic acid. The L-ascorbic acid content was 40 wt. % based on the total weight of the porous microbeads.

2. FILM COATING METHOD OF POROUS MICROBEADS CONTAINING ACTIVE COMPONENTS

EXAMPLE 4

Film coating method of retinol-containing porous microbeads with a silicone mixture of a polysiloxane-based compound.

TABLE 1

Composition of Film Coating Emulsion

| Constituents | Content (wt. %) |
|---|---|
| Hydroxyl-terminated polydimethylsiloxane | 30 |
| Trimethylsilyl-terminated poly(dimethylsiloxane)-co-methylhydrosiloxane | 10 |
| Zinc octoate | 0.5 |
| Emulsifying agent | 5 |
| Distilled water | 55 |
| Acetic acid | Quantum satis |

(1) Tergitol TMN-6 (Union Carbide) was mixed with Igepal CO-850 (GAF) at the mixing ratio of 2:3 and the mixture was stirred to obtain an emulsifying agent.

(2) Trimethylsilyl-terminated poly(dimethylsiloxane)-co-methylhydrosiloxane (48237-4 Aldrich$^R$) was mixed with zinc octoate according to the composition shown in Table 1, under stirring.

(3) The emulsifying agent of step (1) was mixed with the resulting material of step (2).

(4) Acetic acid was added to control the pH of distilled water in the range of 4~5.

(5) The resulting material of step (4) was slowly added to that of step (3) under vigorous stirring, while preventing generation of excessive gas bubbles.

(6) The resulting mixture was emulsified with a homogeneous mixer at 4000 rpm to obtain a film coating emulsion.

100 g of the retinol-containing porous microbeads prepared in Example 1 were added to 900 g of the film coating emulsion prepared by the above method. The resulting material was stirred for about 4 hours and filtered to separate the porous microbeads. The porous microbeads were maintained in a vacuum oven at 40° C. for about 5 hours to yield film coated retinol-containing porous microbeads.

EXAMPLE 5

(1) Film coating method of porous microbeads containing L-ascorbic acid with silicone.

The porous microbeads containing L-ascorbic acid prepared in Example 2 were dispersed in a mixed solution of dimethicone (DC200, consistency 100 CS, Dow Corning) and dichloromethane at the mixing ratio of 1:10. The dimethicone was added in an amount of 20 wt. % based on the total weight of the porous microbeads for film coating. The dispersion solution was subjected to vacuum vaporization under stirring to remove the volatile organic solvent, dichloromethane, and yield powdery porous microbeads film coated with dimethicone. Drying the resulting microbeads under vacuum for one day removed dichloromethane completely and gave film-coated porous microbeads containing L-ascrobic acid.

EXAMPLE 6

(1) Film coating method of porous microbeads containing L-ascorbic acid with a silicone mixture of a polysiloxane-based compound and a silane-based compound.

50 g of hydroxyl-terminated polydimethylsiloxane (Q1-3563, Dow Corning), 3 g of methyltrimethoxysilane and 0.5 g of dibutyltin dilaurate were added to 800 ml of dichloromethane. To the mixed solution were added 50 g of the porous microbeads containing L-ascorbic acid prepared in Example 2. The resulting material was stirred with a paddle mixer for about 2~3 hours and added to a reactor with a condenser, after which it was heated to 40° C. to remove the dichloromethane through vaporization. Then, the porous microbeads were collected and maintained at the room temperature for three days to remove the residual solvent, thus obtaining densely cross-linked porous microbeads containing L-ascorbic acid.

EXAMPLE 7

(2) Film coating method of porous microbeads containing L-ascorbic acid with silicone.

The same procedures as described in Example 5 were performed with an exception that the porous microbeads containing L-ascorbic acid prepared in Example 3 was used instead of those prepared in Example 2. Thus film coated porous microbeads containing L-ascorbic acid were obtained.

EXAMPLE 8

(2) Film coating method of porous microbeads containing L-ascorbic acid with a silicone mixture of a polysiloxane-based compound and a silane-based compound.

The same procedures as described in Example 6 were performed with an exception that the porous microbeads containing L-ascorbic acid prepared in Example 3 was used instead of those prepared in Example 2. Thus film coated porous microbeads containing L-ascorbic acid were obtained.

3. PREPARATION OF W/O TYPE COSMETIC COMPOSITION FOR MEASUREMENT OF STABILIZATION EFFECT

EXAMPLE 9

A w/o (water in oil) type cosmetic composition shown in Table 2 was prepared in order to measure the stabilization effect of the film coated retinol-containing porous microbeads according to Example 4.

TABLE 2

W/O Type Cosmetic Composition

| Constituent | Content (wt. %) |
| --- | --- |
| Stearic acid | 1.0 |
| Cetostearylalcohol | 0.7 |
| Microcrystalline Lead | 0.2 |
| Monostearate glycerin | 0.5 |
| Liquid paraffin | 5.0 |
| Monostearate sorbitan | 0.3 |
| Monostearate polyoxyethylene sorbitan | 1.1 |
| Squalane | 3.5 |
| Purified water | ~100 |
| Concentrated glycerin | 6.5 |
| Carboxyvinyl polymer | 0.12 |
| Hyaluronic acid extract | 0.5 |
| Santan gum | 0.02 |
| Preservative | Quantum satis |
| Scent | Quantum satis |
| Porous microbeads containing active components | 5~20 |

COMPARATIVE EXAMPLE 1

A water in oil type cosmetic composition shown in Table 2 was prepared with the retinol-containing porous microbeads of Example 1, for comparison of the film coated porous microbeads of Example 9 to untreated porous microbeads in regard to the stability of retinol.

EXAMPLE 10

A water in oil type cosmetic composition shown in Table 2 was prepared for measuring stabilization effect of the film coated porous microbeads containing L-ascorbic acid according to Example 5.

EXAMPLE 11

A water in oil type cosmetic composition shown in Table 2 was prepared for measuring stabilization effect of the film coated porous microbeads containing L-ascorbic acid according to Example 6.

COMPARATIVE EXAMPLE 2

A water in oil type cosmetic composition shown in Table 2 was prepared with the porous microbeads containing L-ascorbic acid obtained in Example 2, for comparison of the film coated porous microbeads of Examples 10 and 11 to untreated porous microbeads in regard to the stability of L-ascorbic acid.

Experiment 1: Stability of retinol

For comparison of film coated porous microbeads to untreated ones in regard to the stability of retinol, the water in oil type cosmetic compositions of Example 9 and Comparative Example 1 were exposed to air at 45° C. and the longitudinal potency of retinol contained therein was measured. The results are presented in Table 3.

TABLE 3

Silicone Coating Effect of Microbeads on Stability of retinol

|  | Example 9 (Film-coated with a polysiloxane-based compound) | Comparative Example 1 (Untreated) |
|---|---|---|
| Initial | 3810 | 3700 |
| After 2 weeks | 3560 | 2250 |
| After 4 weeks | 3520 | 1510 |

The values of Table 3 represent the retinol content in terms of IU (International Unit) per 1 g of the microbead-containing cosmetic composition. The analysis for retinol was performed using an HPLC (High Pressure Liquid Chromatography) with a photodiode array.

It can be seen from Table 3 that the retinol has higher stability in the water in oil type cosmetic composition containing the film coated porous microbeads according to the present invention than in the cosmetic composition with untreated porous microbeads.

Experiment 2: Stability of L-ascorbic acid (vitamin C)

For comparison of film coated porous microbeads to untreated ones in regard to the stability of L-ascorbic acid, the water in oil type cosmetic compositions of Examples 10 and 11, and Comparative Example 2 were exposed to air at 45° C. and the longitudinal potency of L-ascorbic acid contained therein was measured. The results are presented in Table 4.

TABLE 4

Silicone Coating Effect of Microbeads on Stability of L-ascorbic acid

|  | Example 10 (Film-coated with silicone) | Example 11 (Film-coated with a mixed solution of a polysiloxane-based compound and a silane-based compound) | Comparative Example 2 (Untreated) |
|---|---|---|---|
| Initial | 4.00 | 4.00 | 4.00 |
| After 2 weeks | 3.91 | 3.88 | 2.29 |
| After 4 weeks | 3.81 | 3.77 | 0.24 |

The values of Table 4 represent the weight percentage of L-ascorbic acid in the cosmetic compositions containing the porous microbeads. The analysis for L-ascorbic acid was performed using an HPLC with a photodiode array.

It can be seen from Table 3 that the L-ascorbic acid has higher stability in the water in oil type cosmetic composition containing the film coated porous microbeads according to the present invention than in the cosmetic composition with untreated porous microbeads.

Experiment 3: Measurement of dermal permeability of L-ascorbic acid

L-ascorbic acid contained in a composition for dermal application may not penetrate into the skin in a case where the surface of porous microbeads is film coated with silicone of very low melting capacity for L-ascorbic acid after adsorption of L-ascorbic acid to the porous microbeads. For testing the dermal permeability of L-ascorbic acid, a cosmetic composition containing 1% L-ascorbic acid was prepared in the same manner as described in Example 10. A 1 $cm^2$ section of the skin obtained from the abdominal region of a Guinea pig was stationed at a Franz diffusion cell. 0.3 ml of the cosmetic composition was applied to the one side of the skin section with the other side in contact with an aqueous solution of 50 wt. % glycerin. The temperature was maintained at the human body temperature, 37° C. After an elapse of 24 hours, the amount of L-ascorbic acid penetrated to the aqueous solution of 50 wt. % glycerin via the skin section was measured using the HPLC, as a result of which about 19% of the initial L-ascorbic acid was detected from the aqueous solution.

For comparison, a cosmetic composition containing 1% L-ascorbic acid was prepared with the untreated porous microbeads of Comparative Example 2 in the same manner as previously described, and applied to the skin section of the Guinea pig. Then, the permeability of L-ascorbic acid was measured under the same conditions as defined above. After an elapse of 24 hours, about 22% of the initial L-ascorbic acid was detected from the aqueous solution.

In sum, the experimental results reveal that film coating the porous microbeads with silicone and its derivatives greatly increased stability of the active components such as L-ascorbic acid in a cosmetic composition but insignificantly affected the dermal permeability of the active components.

As described above, the present invention maintains and enhances stability of the active components contained in cosmetic and pharmaceutical compositions for dermal application, by film coating porous microbeads containing the active components with silicone or its derivatives to form a water repellent film on the surface of the porous microbeads and thereby prevent destruction of the active components in contact with water.

In other words, film coating the surface of the porous microbeads according to the present invention protects the active components lest the physiochemical properties of the external base should affect the stability of the active components.

While the invention has been shown and described with reference to a certain preferred embodiment thereof, it will be understood by those skilled in the art that various changes in form and details may be made therein without departing from the spirit and scope of the invention as defined by the appended claims.

What is claimed is:

1. A composition for use in dermal application, comprising:
    a plurality of particles having an internal structure comprising a plurality of pores;
    a chemical compound contained in the internal structure of the porous particles; and
    a film over each of the particles, the film comprising a compound selected from the group consisting of a silicone, a polysiloxane, and a derivative of a polysiloxane.

2. The composition as defined in claim 1, wherein the silicone is at least one selected from the group consisting of methicone, dimethicone, dimethicone copolyol and its derivatives, dimethiconol and its derivatives, and copolymers of the precedings.

3. The composition as defined in claim 1, wherein the silicone is from about 5 to about 50 wt. % with reference to a total weight of the porous particles.

4. The composition as defined in claim 1, wherein the polysiloxane and the derivative of a polysiloxane have at least one reactive functional group consisting of hydroxyl, halogen and hydrogen.

5. The composition as defined in claim 1, wherein at least one of the polysiloxane and the derivative of a polysiloxane is from about 1 to about 100 wt. % with reference to a total weight of the particles.

6. The composition as defined in claim 1, wherein the film further comprises an alkoxysilane compound.

7. The composition as defined in claim 6, wherein the alkoxysilane compound is less than about 10 wt. % with reference to a total weight of the polysiloxane and the derivative of a polysiloxane.

8. The composition as defined in claim 6, wherein the alkoxysilane compound is selected from the group consisting of tetramethoxysilane, tetraethoxysilane, methyl trimethoxysilane, methacryloxypropyltrimethyoxysilane and glycydoxypropyltrimethoxysilane.

9. The composition as defined in claim 1, wherein the chemical compound comprises a cosmetically or pharmaceutically active ingredient.

10. The composition as defined in claim 9, wherein the chemical compound is vitamins, antioxidants or enzymes.

11. A method of using the composition of claim 1, the method comprising applying the composition onto skin of a human or animal body.

12. A method of making a composition, the method comprising:
   preparing a plurality of particles containing a chemical compound in an internal structure thereof;
   preparing a coating mixture comprising a solvent and a compound selected from the group consisting of a silicone, a polysiloxane, and a derivative of a polysiloxane;
   mixing the plurality of particles with the coating mixture; and
   evaporating the solvent from the coating mixture, thereby forming a film over the particles, said film comprising said compound.

13. The method as defined in claim 12, wherein the chemical compound is water soluble, and the solvent is water-immiscible.

14. The method as defined in claim 13, wherein the water-immiscible solvent is selected from the group consisting of dichloromethane, chloroform, ethyl acetate and acetone.

15. The method as defined in claim 12, wherein the chemical compound is water non-soluble, the solvent is water-miscible.

16. The method as defined in claim 12, wherein zinc octoate and dibutyltin dilaurate are added to the coating mixture as a catalyst in an amount of 0.1~1 wt. % with reference to a total weight of the polysiloxane and the derivative thereof.

17. A composition prepared by the method according to claim 12.

18. The composition as defined in claim 17, wherein the chemical compound comprises a cosmetically or pharmaceutically active ingredient.

* * * * *